United States Patent [19]

Moore

[11] Patent Number: Plant 6,617

[45] Date of Patent: Feb. 21, 1989

[54] ROSE PLANT/VAR.: MORSEGOLD

[75] Inventor: Ralph S. Moore, Visalia, Calif.

[73] Assignee: Sequoia Nursery, Visalia, Calif.

[21] Appl. No.: 91,735

[22] Filed: Aug. 31, 1987

[51] Int. Cl.[4] ..... A01H 5/00

[52] U.S. Cl. ..... Plt./8

[58] Field of Search ..... Plt./8

*Primary Examiner*—James R. Feyrer

[57] ABSTRACT

This invention relates to a new and distinct variety of miniature rose plant primarily identified by its yellow buds and flowers.

1 Drawing Sheet

The present invention relates to a new and distinct variety of hardy, dwarf, bush type rose plant of the miniature class; the variety being primarily characterized—as to novelty—by the double yellow flowers with high centers which generally open to a cupped or rounded form and holds color extremely well.

The variety is further characterized by:

An abundance of bloom, with flowers borne both singly and also several to the stem in small clusters or loose spray.

Some fragrance.

A plant which is vigorous, of rounded to spreading shape with small semi-glossy foliage with pointed leaflets; the buds and flowers being similar in form to Gold Badge (Var:Meigronuri) Floribunda—U.S. Plant Pat. No. 4,625.

The plant, which has a normal height of 10–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery, located at Visalia, Calif., under conditions of careful control and observation, as a cross between an unnamed miniature seedling (Little Darling×Lemon Delight)—not patented, as the seed parent and Gold Badge (Var: Meigronuri) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature. Variety identification: Morsegold (Commercial synonym: Sequoia Gold).

Flowers born: Singly and several together (3 to 5) on sturdy, wirey stems.

Quantity of bloom: Abundant both outside and in greenhouse.

Bud:

*Peduncle.*—Medium length; slender but sturdy; erect; medium green, with numerous small prickles, varying in size and length. Before calyx breaks; size — small.

*Form.*—Pointed, with several small foliaceous apendages and hairs on surface of bud; with foliaceous parts extending beyond the tip of the bud equal to more than one-half of its length. Color — medium green. As calyx breaks, color — yellow. Opening: opens well in all weather.

Bloom:

*Size when fully open.*—Small, averaging about 45–50 mm ($1\frac{3}{4}$–2").

*Petalage.*—Double — averaging about 20–25 petals, arranged, regularly plus several small petaloids.

*Form.*—High centered at first becoming cupped to rounded with petals rolled loosely outward and downward. Open flowers show stamens.

Petals: Fairly thick; satiny on inside and on outside surface.

*Shape.*—Outside petals, broad lanceolate (almost round) with rounded tip and very short acute tip; intermediate — broad lanceolate with nearly round or short acute tin; inside — lanceolate with acute tip.

Color: Newly opened flower from a plant grown in plastic greenhouse (August 1987), Visalia, Calif.

*Outside petal.*—Outside surface — yellow — near Canary Yellow 2/1 at base becoming near Canary Yellow 2/2 near tip. Inside surface — yellow — near Aureolin 3/1, being lighter near petal tip and slightly darker yellow near base.

*Intermediate petal.*—Outside surface similar to outside petal. Inside surface similar to outside petal.

*Inner petal.*—Outside surface — similar to intermediate petal; inside surface — similar to intermediate petal. General color effect; newly opened flowers — bright yellow. Three days open — color-similar to fresh open flower, but less bright. Behavior — opens well in all weather. Spent petals or flowers drop off. Flower longevity (July–August 1987) — plant in pot 6–7 days or longer. Cut flowers at living room temperature 5–7 days.

Note: This variety holds the yellow color better than most other miniatures.

Reproductive organs:

*Stamens.*—Average number, yellow.
*Filaments.*—Medium length — yellow.
*Anthers.*—Yellow.
*Pollen.*'Fair amount.
*Pistils.*—Average number.
*Styles.*—Varying length; yellowish; bunched.
*Ovaries.*—All enclosed in calyx.
*Hips.*—Several — orange when ripe.
*Sepals.*—Permanent; spear shaped; recurved.
*Seed.*—Several.

Foliage:

*Leaves.*—Compound of five (sometimes three or seven) leaflets; medium small; leathery; semi-glossy to matt.

*Leaflets.*—Shape; broad lanceolate; apex acute; base — acute — sometimes rounded; serrated. Color: Medium green; new growth — normal (medium) green. Rachis: Medium strength; upper side may have a few very short hairs; grooved; underside may have several small thorns (or claws) and few to several tiny short prickles. Stipules: Medium to long length; medium width; medium to short length narrow points which turn out usually at about 45 degrees or more.

Growth:

*Habit.*—Dwarf; bushy; rounded; much branched.
*Growth.*—Vigorous; internodes short.

*Canes.*—Medium; slender, sturdy.
*Main stems.*—Color: medium green.
*Thorns.*—Average number, of varying size and length — usually straight — inclined slightly downward. Hairs — few or none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described, characterized by buds and flowers of rich medium yellow coloring, the bud being pointed in the early opening stage, resembling in form Gold Badge (Var: Meigronui) Floribunda—U.S. Plant Pat. No. 4,625, with the open flower being fairly double and rounded with about 20–25 petals; and further characterized by a plant of compact, vigorous, well rounded shape, with main stems and shoots of average thorniness, the said plant being easy to propagate from soft wood cuttings and with an abundance of small semi-glossy foliage, the flowers being borne singly or several together in clusters on medium to short length stems.

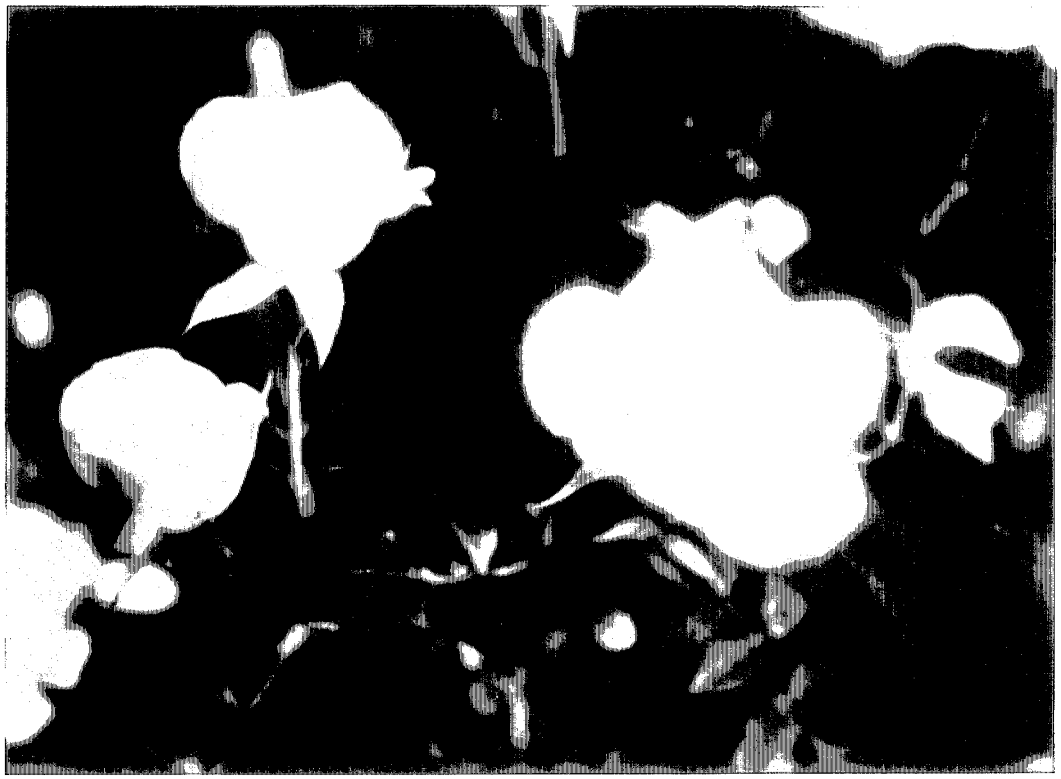

* * * * *